United States Patent
Inada et al.

(10) Patent No.: US 7,488,466 B2
(45) Date of Patent: Feb. 10, 2009

(54) PREPARATION FOR DETERMINING PYRIMIDINE METABOLIC CAPACITY

(75) Inventors: Makoto Inada, Tokushima-ken (JP); Nobuhiro Ikei, Tokushima (JP); Hideji Nonomura, Tokushima-ken (JP); Yasuo Irie, Woburn, MA (US)

(73) Assignee: Otsuka Pharmaceutical Co., Ltd., Tokyo-to (JP)

( * ) Notice: Subject to any disclaimer, the term of this patent is extended or adjusted under 35 U.S.C. 154(b) by 0 days.

(21) Appl. No.: 10/208,851

(22) Filed: Aug. 1, 2002

(65) Prior Publication Data

US 2003/0068272 A1    Apr. 10, 2003

(51) Int. Cl.
*A61K 51/00* (2006.01)
*A61M 36/14* (2006.01)

(52) U.S. Cl. .................... 424/1.81; 424/1.11; 424/1.65; 424/1.73; 424/9.2

(58) Field of Classification Search ................ 424/1.65, 424/1.81, 9.1, 9.2, 9.3, 1.73, 1.11, 94.1; 436/173; 435/183
See application file for complete search history.

(56) References Cited

U.S. PATENT DOCUMENTS

| 5,077,034 A | 12/1991 | Kassis et al. |
| 5,248,771 A | 9/1993 | Dougan |
| 5,944,670 A * | 8/1999 | Katzman ................ 600/543 |
| 6,232,448 B1 | 5/2001 | Yoshikubo et al. ...... 530/388.26 |

OTHER PUBLICATIONS

Creasey et al., "The metabolism of uracil-2-$^{14}$C and the granulocyte response to endotoxin as indicators of the toxicity produced in patients receiving 5-fluorouracil," *Clinical Pharmacology and Therapeutics*, vol. 8, No. 2:273-282, 1967.

Fernandez-Salguero et al., "Correlation between catalytic activity and protein content for the polymorphically expressed dihydropyrimidine dehydrogenase in human lymphocytes," *Biochemical Pharmacology*, vol. 50, No. 7:1015-1020 (1995).

Fleming et al., "Correlation between Dihydropyrimidine Dehydrogenase Activity in Peripheral Mononuclear Cells and Systemic Clearance of Fluorouracil in Cancer Patients," *Cancer Research*, vol. 52:2899-2902 (May 15, 1999).

Johnson, et al., "Semi-automated radioassay for determination of dihydropyrimidine dehydrogenase (DPD) activity; Screening cancer patients for DPD deficiency, a condition associated with 5-fluorouracil toxicity," *Journal of Chromatography B*, vol. 696:183-191 (1997).

(Continued)

*Primary Examiner*—D. L Jones
(74) *Attorney, Agent, or Firm*—Finnegan, Henderson, Farabow, Garrett & Dunner, L.L.P.

(57) ABSTRACT

The present invention provide a method for measuring and assessing the capacity in an individual subject to metabolize a variety of fluorouracil drugs, such as 5-fluorouracil, which are degraded in the pyrimidine metabolic pathway, and a preparation useful for the measurement and assessment. The present invention can be carried out by: administering a preparation for determining pyrimidine metabolic capacity comprising as an active ingredient a pyrimidine compound or pyrimidine metabolic compound that acts as a substrate for a pyrimidine metabolizing enzyme, in which at least one of the carbon, oxygen, and nitrogen atoms is labeled with an isotope; and assessing in vivo pyrimidine metabolic capacity based on the behavior of an excreted metabolite.

11 Claims, 6 Drawing Sheets

| 5-FU | : 5-Fluorouracil |
| FDHU | : Fluorodihydrouracil |
| F-β-UPA | : Fluoro-β-ureidopropionic acid |
| F-β-alanine | : Fluoro-β-alanine |
| DPD | : Dihydropyrimidine dehydrogenase |
| DHPase | : Dihydropyrimidinase |
| β-UPase | : β-Ureidopropionase |

OTHER PUBLICATIONS

Sumi et al., "Automated screening system for purine and pyrimidine metabolism disorders using high-performance liquid chromatography," *Journal of Chromatography B*, vol. 672:233-239 (1995).

Sumi et al., "Possible prediction of adverse reactions to fluorouracil by the measurement of urinary dihydrothymine and thymine," *Int'l. Journal of Molecular Medicine*, vol. 2:477-482 (1998).

Ma et al., "Study of the Use of Fluorouracil Suppositories as Supplementary Presurgical Chemotherapy For Rectal Cancer" China Pharmaceutical Journal, 29:7 pp. 1-9, Jul. 1994.

Ma Lie, Wang, Yi-chun, Supplemental suppository fluorouracil in chemotherapy of rectal cancer, 29 (7); pp. 133-435, Jul. 1994, (non-English).

First Office Action from Patent Office of China for Chinese Application 02806426.7 dated Nov. 19, 2004, (non-English).

Visser et al., "An Optimized Synthesis of [18]F-Labelled 5-Fluorouracil and a Reevaluation of Its Use as a Prognostic Agent," *European Journal of Nuclear Medicine* 15(5):225-229 (1989).

Tanigawa et al., "Simple and Rapid Quantitative Assay of $^{13}$C-labelled Urea in Human Serum Using Liquid Chromatoghapy-Atmospheric Pressure Chemical Ionization Mass Spectrometry," *Journal of Chromatography B.: Biomedical Applications* 683(2):135-142 (1996).

Visser et al., "$^{18}$F-Radiopharmacokinetics of [$^{18}$F]-5-Fluorouracil in a Mouse Bearing Two Colon Tumors with a Different 5-Fluorouracil Sensitivity: A Study for a Correlation with Oncological Results," *Nuclear Medicine and Biology* 23(3):333-342 (1996).

Harris et al., "Relationship Between Dihydropyrimidine Dehydrogenase Activity and Plasma 5-Fluorouracil Levels with Evidence for Circadian Variation of Enzyme Activity and Plasma Drug Levels in Cancer Patients Receiving 5-Fluorouracil by Protracted Continuous Infusion," *Cancer Research* 50(1):197-201 (1990).

European Search Report for European Application No. 02705125.9-2123 (PCT/JP0202351) dated May 21, 2007.

* cited by examiner

FIG. 1

5-FU       : 5-Fluorouracil
FDHU       : Fluorodihydrouracil
F-ß-UPA    : Fluoro-ß-ureidopropionic acid
F-ß-alanine : Fluoro-ß-alanine
DPD        : Dihydropyrimidine dehydrogenase
DHPase     : Dihydropyrimidinase
ß-UPase    : ß-Ureidopropionase

PREPARATION FOR DETERMINING PYRIMIDINE METABOLIC CAPACITY

TECHNICAL FIELD

The present invention relates to a preparation that can be effectively used for determining and assessing pyrimidine metabolic capacity, i.e., the existence, nonexistence, degree, or the like of pyrimidine metabolic disorder, in an individual subject. More specifically, the present invention relates to a preparation for easily determining the capacity in an individual subject to metabolize various fluorouracil drugs, such as 5-fluorouracil, etc., using the expired air or the like. Further, the present invention relates to use of the preparation.

BACKGROUND ART 5-fluorouracil (hereinafter sometimes referred to as "5-FU") and its derivatives (such as tegafur, carmofur, and doxifluridine) are fluorouracil drugs that are most widely used as anticancer drugs at present.

Figure 1:
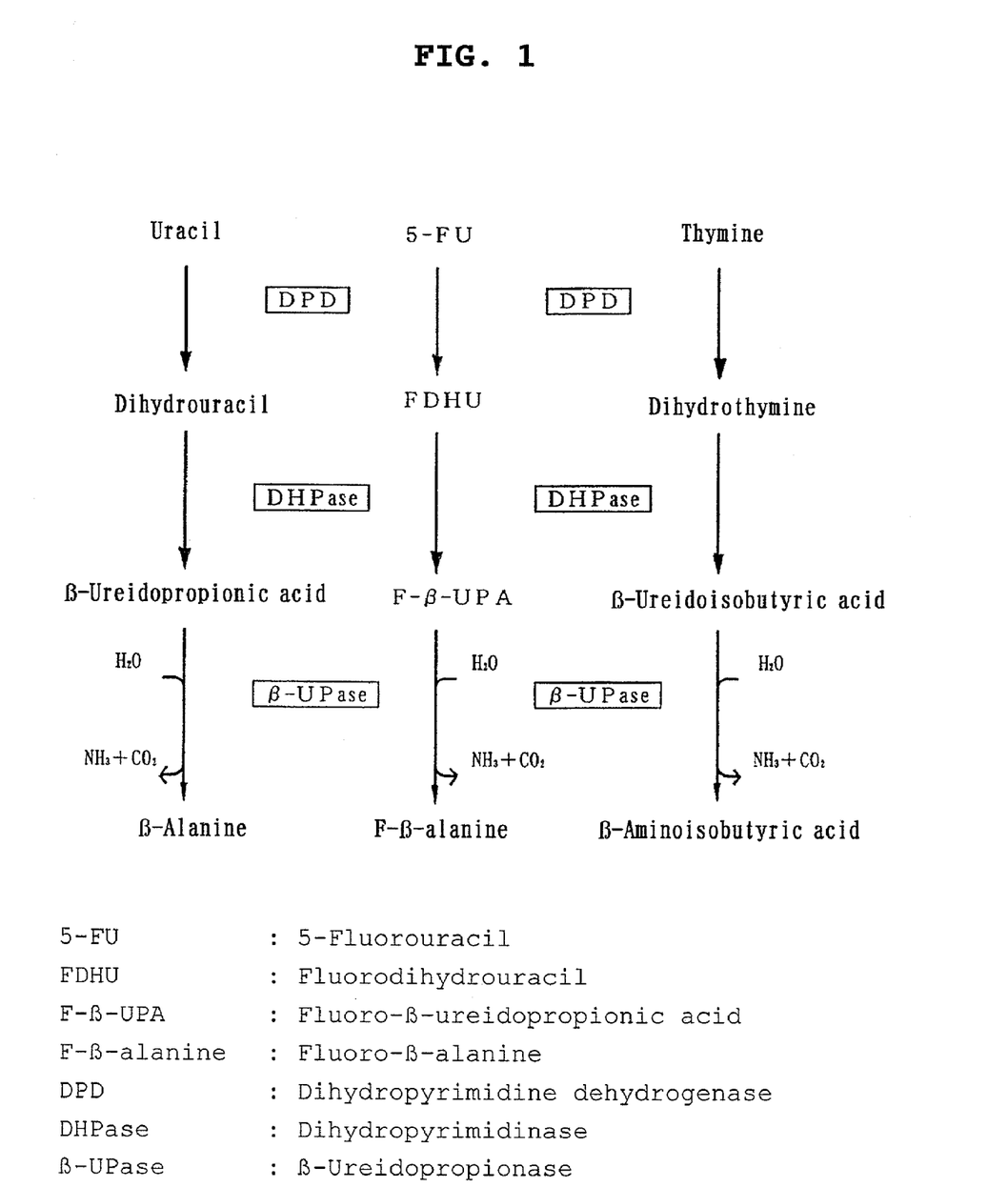
FIG. 1 shows the degradation behavior (metabolic behavior) of pyrimidine compounds (uracil, 5-fluorouracil (5-FU), and thymine) by a series of pyrimidine metabolizing enzymes (dihydropyrimidine dehydrogenase (DPD), dihydropyrimidinase (DHPase), and β-ureidopropionase (β-UPase)).

5-FU is degraded and inactivated mainly by the actions of a series of pyrimidine metabolizing enzymes in the pyrimidine metabolic pathway in the liver. Specifically stated, as shown in FIG. 1, 5-FU administered to the body is metabolized first into 5-fluoro-dihydrouracil (hereinafter sometimes referred to as "FDHU") by the action of dihydropyrimidine dehydrogenase (hereinafter sometimes referred to as "DPD"), which is the first enzyme in the pyrimidine metabolic pathway; and then into fluoro-β-ureidopropionic acid (hereinafter sometimes referred to as "F-β-UPA") by the action of dihydropyrimidinase (hereinafter sometimes referred to as "DHPase"), which is the second enzyme in the pyrimidine metabolic pathway; and then into fluoro-β-alanine (hereinafter sometimes referred to as "F-β-alanine") and carbon dioxide (final metabolites) by the action of β-ureidopropionase (hereinafter sometimes referred to as "β-UPase"; which is the third enzyme in the pyrimidine metabolic pathway.

It has been reported that about 80% of 5-FU administered to the body is degraded in the pyrimidine metabolic pathway (Cancer (Phila), 68, 499-501, 1991), and that DPD (first enzyme) is the rate-limiting enzyme in this metabolic pathway (Cancer Res., 47: 2203-2206, 1987). Accordingly, the administration of 5-FU or another fluorouracil drug to a subject with DPD deficiency or DPD activity reduction is likely to result in abnormally high fluorouracil drug concentration in the blood, thus causing severe side effects (e.g., myelosuppression, digestive symptoms, or the like), because the fluorouracil is not normally metabolized (Cancer Inves. 11 (2): 239-240, 1993). Further, it is known that DPD activity greatly varies individually, and is also different between the sexes (J. Clin. Oncol., 12: 2248-2253, 1994; Adv. Exp. Med. Biol., 431: 811-816, 1998).

Thus, in Europe and America, the necessity of diagnosing the existence, nonexistence, or degree of pyrimidine metabolic disorder, especially a pyrimidine metabolic disorder caused by DPD deficiency and DPD activity reduction, in an individual subject. is urged, to prevent the side effects of 5-FU and other fluorouracil drugs.

There is an established DPD deficiency diagnosis method, wherein the DPD activity of peripheral blood mononuclear cells is determined (Cancer Res., 53: 5433-5438, 1993; Phermacogenetics. 4: 301-306. 1994; J. Inherited. Metab. Dis., 16: 574-576, 1993). However, the method is not suitable for diagnosing cancer patients, who are the subjects to be given fluorouracil drugs, since the method involves use of radioactive substances and complicated pretreatment.

Recent progresses in genetic analysis techniques have facilitated diagnosis of DPD gene deficiency. Further, a number of reports have been made on polymorphism of the DPD gene, which may cause DPD activity reduction. However, the correlation between the DPD gene polymorphism and DPD activity has not been elucidated yet. Thus, it is extremely difficult to assess the existence or nonexistence of DPD activity, in particular the degree of DPD activity, on the basis of the genetic information.

In the present situation where fluorouracil drugs have proved effective in anticancer therapy and are often enhanced by a variety of drugs that inhibit the enzymatic activity of DPD (a metabolizing enzyme for fluorouracil drugs), there is a demand for the development of a simple method for diagnosing the pyrimidine metabolic capacity, i.e., the existence, nonexistence, or degree of pyrimidine metabolic disorder, in a subject beforehand, to predict and prevent the side effects that may be caused by fluorouracil drug therapy.

DISCLOSURE OF THE INVENTION

In view of the above situation, the first object of the present invention is to provide a preparation for easily determining and assessing the pyrimidine metabolic capacity in an individual subject. Specifically, the first object is to provide a preparation useful for determining the pyrimidine metabolic behavior in an individual subject and easily assessing the metabolic capacity, i.e., the existence, nonexistence, or degree of pyrimidine metabolic disorder, in the subject.

The second object of the present invention is to provide a method for determining the pyrimidine metabolic behavior in an individual subject and easily assessing the metabolic capacity, i.e., the existence, nonexistence, or degree of pyrimidine metabolic disorder, in the subject.

The third object of the present invention is to provide a method for screening a subject for suitability for fluorouracil drug administration.

The present inventors found that the pyrimidine metabolic capacity, i.e., the existence, nonexistence, or degree of pyrimidine metabolic disorder, in a subject can be easily assessed by administering an isotope-labeled pyrimidine compound to the subject and measuring the excretion behavior (including excretion amount, excretion rate, and change in the amount and rate with the lapse of time) of isotope-labeled $CO_2$ in the expired air. Based on these findings, the inventors were convinced of the following: It is possible to screen subjects for suitability for the administration of a fluorouracil drug, such as 5-FU, etc., by excluding subjects for whom/which the therapeutic effects of the fluorouracil drug cannot be expected because of their extremely high pyrimidine metabolic capacity, and those for whom/which the side effects of the fluorouracil drug are feared because of their extremely low pyrimidine metabolic capacity, based on the results of the determination of the pyrimidine metabolic behavior in individual subjects using the above-mentioned isotope-labeled pyrimidine compound. Further, it is possible to assess the clearance of a fluorouracil drug and establish a more effective dosage regimen (formula, dose, number of doses, etc.) of the fluorouracil drug for individual subjects based on the pyrimidine metabolic capacity in these subjects. The present invention has been accomplished based on these findings.

The present invention provides the preparations for determining pyrimidine metabolic capacity, described in the following items 1 to 8:

1. A preparation for determining pyrimidine metabolic capacity, comprising as an active ingredient a pyrimidine compound or pyrimidine metabolic compound in which at least one of the carbon, oxygen, and nitrogen atoms is labeled with an isotope.

1-1. A preparation for determining pyrimidine metabolic capacity, comprising as an active ingredient a pyrimidine compound or pyrimidine metabolic compound in which at least one of the carbon, oxygen, and nitrogen atoms is labeled with an isotope, and a pharmaceutically acceptable carrier.

2. The preparation according to item 1, wherein the pyrimidine compound is a substrate for dihydropyrimidine dehydrogenase, which is a pyrimidine metabolizing enzyme, or a precursor of the substrate.

3. The preparation according to item 1, wherein the pyrimidine metabolic compound is a substrate for dihydropyrimidinase or β-ureidopropionase, either of which is a pyrimidine metabolizing enzyme.

4. The preparation according to item 1 or 2, wherein the pyrimidine compound is at least one member selected from the group consisting of uracil, 5-fluorouracil, and thymine.

5. The preparation according to item 1 or 2, wherein the pyrimidine compound is at least one precursor of substrate for dihydropyrimidine dehydrogenase, selected from the group consisting of doxifluridine, tegafur, and carmofur.

6. The preparation according to item 1 or 3, wherein the pyrimidine metabolic compound is at least one member selected from the group consisting of dihydrouracil, 5-fluorodihydrouracil, dihydrothymine, β-ureidopropionic acid, fluoro-β-ureidopropionic acid, and βureidoisobutyric acid.

7. The preparation according to any one of items 1 to 6, comprising as an active ingredient a pyrimidine compound or pyrimidine metabolic compound in which at least one of the carbon and oxygen atoms is labeled with an isotope, the preparation being capable of producing isotope-labeled $CO_2$ after administration to a subject.

8. The preparation according to any one of items 1 to 7, wherein the isotope is at least one member selected from the group consisting of $^{13}C$, $^{14}C$, $^{18}O$, and $^{5}N$.

The preparation for determining pyrimidine metabolic capacity according to the present invention is used to determine and assess the pyrimidine metabolic capacity in an individual subject by measuring the metabolic behavior of a pyrimidine compound or pyrimidine metabolic compound, in particular the excretion behavior of a metabolite of such a compound (including excretion amount, excretion rate, and change in the amount and rate with the lapse of time), in the subject (these behaviors being hereinafter sometimes referred to as "pyrimidine metabolic behavior"). Therefore, the preparation for determining pyrimidine metabolic capacity of the present invention can also be expressed as a preparation for determining pyrimidine metabolic behavior.

The present invention further provides the methods for determining pyrimidine metabolic capacity, described in the following items 9 to 10-1:

9. A method for determining pyrimidine metabolic capacity, comprising the steps of administering a preparation according to any one of items 1 to 8 to a subject, and measuring the excretion behavior of an isotope-labeled metabolite excreted from the body.

9-1. The method for determining pyrimidine metabolic capacity according to item 9, wherein the isotope-labeled metabolite is at least one member selected from the group consisting of isotope-labeled $CO_2$, isotope-labeled β-alanine, isotope-labeled fluoro-β-alanine, and isotope-labeled β-aminoisobutyric acid.

10. A method for determining pyrimidine metabolic capacity, comprising the steps of administering a preparation according to any one of items 1 to 8 to a subject, and measuring the excretion behavior of isotope-labeled $CO_2$ in the expired air.

10-1. The method according to item 10, wherein a preparation of item 4 is used as the preparation for determining pyrimidine metabolic capacity.

The above methods for determining pyrimidine metabolic capacity can also be expressed as methods for determining pyrimidine metabolic behavior, since the methods are carried out by measuring the excretion behavior of a metabolite of a pyrimidine compound or pyrimidine metabolic compound (pyrimidine metabolic behavior).

The present invention also provides the methods for assessing pyrimidine metabolic capacity, described in the following items 11 to 12-2:

11. The method for assessing the pyrimidine metabolic capacity in a subject, comprising the steps of administering a preparation according to any one of items 1 to 8 to the subject, measuring the excretion behavior of an isotope-labeled metabolite excreted from the body, and assessing the obtained excretion behavior in the subject.

11-1. The method according to item 11, wherein the isotope-labeled metabolite is at least one member selected from the group consisting of isotope-labeled $CO_2$, isotope-labeled β-alanine, isotope-labeled fluoro-β-alanine, and isotope-labeled β-aminoisobutyric acid.

11-2. The method according to item 11 or 11-1, wherein the excretion behavior in the subject is assessed by comparison with the corresponding excretion behavior in a healthy subject with a normal pyrimidine metabolic capacity.

12. A method for assessing the pyrimidine metabolic capacity in a subject, comprising the steps of administering a preparation according to any one of items 1 to 8 to the subject, measuring the excretion behavior of isotope-labeled $CO_2$ in the expired air, and assessing the obtained excretion behavior in the subject.

12-1. The method according to item 12, wherein a preparation of item 4 is used as the preparation for determining pyrimidine metabolic capacity.

12-2. The method according to item 12 or 12-1, wherein the excretion behavior in the subject is assessed by comparison with the corresponding excretion behavior in a healthy subject with a normal pyrimidine metabolic capacity.

The present invention also provides the methods for determining the existence, nonexistence, or degree of pyrimidine metabolic disorder in a subject, described in the following items 13 to 14-1:

13. A method for determining the existence, nonexistence, or degree of pyrimidine metabolic disorder in a subject, comprising the steps of administering a preparation according to any one of items 1 to 8 to the subject, measuring the excretion behavior of an isotope-labeled metabolite, and comparing the obtained excretion behavior in the subject with the corresponding excretion behavior in a healthy subject with a normal pyrimidine metabolic capacity.

13-1. The method according to item 13, wherein the isotope-labeled metabolite is at least one member selected from the group consisting of isotope-labeled $CO_2$, isotope-labeled β-alanine, isotope-labeled fluoro-β-alanine, and isotope-labeled β-aminoisobutyric acid.

14. A method for determining the existence, nonexistence, or degree of pyrimidine metabolic disorder in a subject, comprising the steps of administering a preparation according to any one of items 1 to 8 to the subject, measuring the excretion behavior of isotope-labeled $CO_2$ in the expired air, and comparing the obtained $CO_2$ excretion behavior in the subject with the corresponding excretion behavior in a healthy subject with a normal pyrimidine metabolic capacity.

14-1. The method according to item 14, wherein a preparation of item 4 is used as the preparation for determining pyrimidine metabolic capacity.

The present invention further provides the methods for screening a subject for suitability for fluorouracil drug administration, described in the following items 15 to 17.

15. The method for screening a subject for suitability for fluorouracil drug administration, comprising the steps of administering a preparation according to any one of items 1 to 8 to the subject, measuring the excretion behavior of an isotope-labeled metabolite, and determining suitability for fluorouracil drug administration based on the obtained excretion behavior in the subject.

15-1. The method according to item 15, wherein the isotope-labeled metabolite is at least one member selected from the group consisting of isotope-labeled $CO_2$, isotope-labeled β-alanine, isotope-labeled fluoro-β-alanine, and isotope-labeled β-aminoisobutyric acid.

15-2. The method according to item 15 or 15-1, wherein the suitability for fluorouracil drug administration is determined by comparing the excretion behavior in the subject or a pharmacokinetic parameter obtained therefrom with the corresponding excretion behavior or pharmacokinetic parameter in a healthy subject with a normal pyrimidine metabolic capacity.

16. A method for screening a subject for suitability for fluorouracil drug administration, comprising the steps of administering a preparation according to any one of items 1 to 8 to the subject, measuring the excretion behavior of isotope-labeled $CO_2$ excreted in the expired air, and determining suitability for fluorouracil administration based on the obtained $CO_2$ excretion behavior in the subject.

16-1. The method according to item 16, wherein a preparation according to item 4 is used as the preparation for determining pyrimidine metabolic capacity.

16-2. The method according to item 16 or 16-1, wherein the suitability for fluorouracil drug administration is determined by comparing the $CO_2$ excretion behavior in the subject or a pharmacokinetic parameter obtained therefrom with the corresponding $CO_2$ excretion behavior or pharmacokinetic parameter in a healthy subject with a normal pyrimidine metabolic capacity.

17. The method according to any one of items 15 to 16-2, wherein the fluorouracil drug is an anticancer drug selected from the group consisting of 5-fluorouracil, tegafur, carmofur, and doxifluridine.

Furthermore, the present invention includes the following embodiments:

18. A method for assessing the clearance of a fluorouracil drug in a subject, comprising the steps of administering a preparation according to any one of items 1 to 8 to the subject, measuring the excretion behavior of an isotope-labeled metabolite, and assessing the clearance of the fluorouracil drug in the subject based on the obtained excretion behavior.

19. A method for establishing a dosage regimen of a fluorouracil drug for a subject, comprising the steps of administering a preparation according to any one of items 1 to 8 to the subject, measuring the excretion behavior of an isotope-labeled metabolite, assessing the pyrimidine metabolic capacity in the subject based on the obtained excretion behavior, and establishing a dosage regimen (formula, dose, number of doses, dosing frequency, etc.) of a fluorouracil drug for the subject based on the pyrimidine metabolic capacity.

20. Use of a pyrimidine compound or pyrimidine metabolic compound in which at least one of the carbon, oxygen, and nitrogen atoms is labeled with an isotope, for producing a preparation for determining pyrimidine metabolic capacity.

21. Use of a pyrimidine compound or pyrimidine metabolic compound in which at least one of the carbon, oxygen, and nitrogen atoms is labeled with an isotope, or a composition comprising the pyrimidine compound or pyrimidine metabolic compound as an active ingredient, for determining the pyrimidine metabolic capacity in a subject.

21-1. Use of a composition comprising as an active ingredient a pyrimidine compound or pyrimidine metabolic compound in which at least one of the carbon, oxygen, and nitrogen atoms is labeled with an isotope, and a pharmaceutically acceptable carrier, for determining the pyrimidine metabolic capacity in a subject.

22. Use of a pyrimidine compound or pyrimidine metabolic compound in which at least one of the carbon, oxygen, and nitrogen atoms is labeled with an isotope, or a composition comprising the pyrimidine compound or pyrimidine metabolic compound as an active ingredient, for assessing the pyrimidine metabolic capacity in a subject.

22-1. Use of a composition comprising as an active ingredient a pyrimidine compound or pyrimidine metabolic compound in which at least one of the carbon, oxygen, and nitrogen atoms is labeled with an isotope, and a pharmaceutically acceptable carrier, for assessing the pyrimidine metabolic capacity in a subject.

23. Use of a pyrimidine compound or pyrimidine metabolic compound in which at least one of the carbon, oxygen, and nitrogen atoms is labeled with an isotope, or a composition comprising the pyrimidine compound or pyrimidine metabolic compound as an active ingredient, for determining the existence, nonexistence, or degree of pyrimidine metabolic disorder in a subject.

23-1. Use of a composition comprising as an active ingredient a pyrimidine compound or pyrimidine metabolic compound in which at least one of the carbon, oxygen, and nitrogen atoms is labeled with an isotope, and a pharmaceutically acceptable carrier, for determining the existence, nonexistence, or degree of pyrimidine metabolic disorder in a subject.

24. Use of a pyrimidine compound or pyrimidine metabolic compound in which at least one of the carbon, oxygen, and nitrogen atoms is labeled with an isotope, or a composition comprising the pyrimidine compound or pyrimidine metabolic compound as an active ingredient, for assessing the clearance of a fluorouracil drug in a subject.

24-1. Use of a composition comprising as an active ingredient a pyrimidine compound or pyrimidine metabolic compound in which at least one of the carbon, oxygen, and nitrogen atoms is labeled with an isotope, and a pharmaceutically acceptable carrier, for assessing the clearance of a fluorouracil drug in a subject.

25. Use of a pyrimidine compound or pyrimidine metabolic compound in which at least one of the carbon, oxygen, and nitrogen atoms is labeled with an isotope, or a composition comprising the pyrimidine compound or pyrimidine metabolic compound as an active ingredient, for establishing a dosage regimen of a fluorouracil drug for a subject.

25-1. Use of a composition comprising as an active ingredient a pyrimidine compound or pyrimidine metabolic compound in which at least one of the carbon, oxygen, and nitrogen atoms is labeled with an isotope, and a pharmaceutically acceptable carrier, for establishing a dosage regimen of a fluorouracil drug for a subject.

As used herein, "pyrimidine metabolic pathway" means an in vivo catabolic pathway participating in the degradation of a series of compounds having a pyrimidine skeleton, such as pyrimidine. The enzymes participating in the degradation reactions in the pyrimidine metabolic pathway is referred to as "pyrimidine metabolizing enzyme". The "pyrimidine metabolizing enzyme" means both an individual enzyme participating in each degradation reaction in the pyrimidine metabolic pathway, and a series of enzymes involved in the pyrimidine metabolic pathway. As shown in FIG. 1, a compound having a pyrimidine skeleton (hereinafter sometimes referred to as "pyrimidine compound"), such as uracil, 5-fluorouracil, thymine, etc., is converted to the final metabolites through three enzyme reactions in the pyrimidine metabolic pathway. Also as used herein, "final metabolite" and "metabolite" mean a final product produced through the series of enzyme reactions in the pyrimidine metabolic pathway. On the other hand, a product produced by an enzyme reaction during the metabolic pathway is referred to as "intermediate metabolite".

BEST MODE FOR CARRYING OUT THE INVENTION (1) Preparation for Determining Pyrimidine Metabolic Capacity The preparation for determining pyrimidine metabolic capacity according to the present invention comprises, as an active ingredient, a pyrimidine compound in which at least one of the carbon, oxygen and nitrogen atoms is labeled with an isotope.

Pyrimidine compounds usable in the present invention include a wide variety of compounds having a pyrimidine skeleton, and are preferably those that act as substrates for pyrimidine metabolizing enzymes, especially for dihydropyrimidine dehydrogenase (DPD), i.e., the first enzyme in the pyrimidine metabolic pathway in vivo. Specific examples of such pyrimidine compounds include uracil, thymine, and their derivatives. Any derivative can be used without limitation as long as it acts as a substrate for DPD, and is converted to a final metabolite through the pyrimidine metabolic pathway and excreted in the expired air or urine. Specific examples of such derivatives include halides of uracil, such as 5-fluorouracil and 5-bromouracil, and the like. Preferred examples of pyrimidine compounds include uracil, thymine, and 5- fluorouracil.

Useful pyrimidine compounds include, in addition to the above compounds acting as direct substrates for DPD, compounds that act as indirect substrates for the enzyme, i.e., precursors (including prodrugs), which are metabolized or degraded in vivo into substrates for DPD (such as uracil, thymine, and 5-fluorouracil). Examples of such precursors include precursors of uracil, such as cytosine, uridine, and phosphates thereof (e.g., uridylic acid); precursors of thymine, such as 5-methylcytosine, thymidine, and phosphates thereof (e.g., thymidylic acid); and precursors (prodrugs) of 5-fluorouracil, such as tegafur, carmofur, doxifluridine, etc.

The preparation of the present invention may comprise, in place of the pyrimidine compound, a compound corresponding to an intermediate metabolite of a pyrimidine compound (hereinafter sometimes referred to as "pyrimidine metabolic compound") as an active ingredient. Examples of such pyrimidine metabolic compounds include compounds that act as substrates for DHPase (the second enzyme in the pyrimidine metabolic pathway), such as dihydrouracil, dihydrothymine, and their derivatives (e.g., halides of dihydrouracil, such as 5-fluorodihydrouracil) (these compounds being hereinafter sometimes referred to as "first metabolic compounds"); and compounds that act as substrates for β-UPase (the third enzyme in the pyrimidine metabolic pathway), such as β-ureidopropionic acid, β-ureidoisobutyric acid, and their derivatives (e.g., halides of β-ureidopropionic acid, such as fluoro-β-ureidopropionic acid (these compounds being hereinafter sometimes referred to as "second metabolic compounds").

These pyrimidine compounds or pyrimidine metabolic compounds for use as active ingredients of the preparation for determining pyrimidine metabolic capacity are characterized in that at least one of the carbon, oxygen and nitrogen atoms in the molecule is labeled with an isotope. The isotope is not limited, and specific examples of the isotope include $^{13}$C, $^{14}$C, $^{18}$O, $^{15}$N, and the like. The isotope may be radioactive or non-radioactive, but non-radioactive $^{13}$C, $^{18}$O, or $^{15}$N is preferred from the safety point of view.

The pyrimidine compound or pyrimidine metabolic compound for use in the present invention may have one isotope in the molecule or may have two or more isotopes of the same or different elements. Although not limitative, it is preferable that a carbon atom or (an) oxygen atom(s) in the pyrimidine compound or pyrimidine metabolic compound be labeled so that at least part (C or O) of $CO_2$ produced through the pyrimidine metabolic pathway is labeled with an isotope. Examples of such compounds include those having isotope-labeled carbon at the 2-position of the pyrimidine skeleton. Specific examples include 2-$^{13}$C-labeled uracil, 2-$^{13}$C-labeled fluorouracil, and the like.

The method for labeling a pyrimidine compound or pyrimidine metabolic compound with such an isotope is not limited and may be a conventional method (Sasaki, "5.1 Application of Stable Isotopes in Clinical Diagnosis": Kagaku no Ryoiki (Journal of Japanese Chemistry) 107, "Application of Stable Isotopes in Medicine, Pharmacy, and Biology", pp. 149-163 (1975), Nankodo: Kajiwara, RADIOISOTOPES, 41, 45-48 (1992), etc.). Some pyrimidine compounds and pyrimidine metabolic compounds labeled with these isotopes are commercially available, and these commercial products are conveniently usable.

The preparation of the present invention may be in any form suitable for the purposes of the present invention. Examples of suitable forms include injections, intravenous injections, suppositories, eye drops, nasal solutions, and other parenteral forms; and solutions (including syrups), suspensions, emulsions, tablets (either uncoated or coated), capsules, pills, powders, subtle granules, granules, and other oral forms.

The preparation of the present invention may consist substantially of the isotope-labeled pyrimidine compound or pyrimidine metabolic compound as an active ingredient, but may be a composition further containing a pharmaceutically acceptable carrier or additive generally used in this field according to the form of the preparation (dosage form) (composition for determining pyrimidine metabolic capacity), as long as the actions and effects of the preparation of the present invention are not impaired.

In such a composition, the proportion of the isotope-labeled pyrimidine compound or pyrimidine metabolic compound as an active ingredient is not limited and may be 1 to 95 wt. % in 100 wt. % of the composition. The proportion can be suitably adjusted within the above range.

For example, when the above composition is formed into tablets, useful carriers include, for example, lactose, sucrose, sodium chloride, glucose, urea, starches, calcium carbonate, kaolin, crystalline cellulose, silicic acid, and other excipients; simple syrups, glucose solutions, starch solutions, gelatin solutions, carboxymethyl cellulose, shellac, methyl cellulose, potassium phosphate, polyvinyl pyrrolidone, and other binders; dry starches, sodium alginate, agar powder, laminaran powder, sodium hydrogencarbonate, calcium carbonate, polyoxyethylene sorbitanfatty acid esters, sodium lauryl sulfate, stearic acid monoglyceride, starches, lactose, and other disintegrators; sucrose, stearic acid, cacao butter, hydrogenated oils, and other disintegration inhibitors; quaternary ammonium bases, sodium lauryl sulfate, and other absorption accelerators; glycerin, starches, and other humectants; starches, lactose, kaolin, bentonite, colloidal silicic acid, and other adsorbents; and purified talc, stearate, boric acid powder, polyethylene glycol, and other lubricants. Further, the tablets may be those with ordinary coatings (such as sugar-coated tablets, gelatin-coated tablets, or film-coated tablets), double-layer tablets, or multi-layer tablets.

When forming the composition for determining pyrimidine metabolic capacity into pills, useful carriers include, for example, glucose, lactose, starches, cacao butter, hydrogenated vegetable oils, kaolin, talc, and other excipients; gum arabic powder, tragacanth powder, gelatin, and other binders; and laminaran, agar, and other disintegrators.

Capsules are prepared in a routine manner, by mixing the active ingredient according to the present invention with any of the above carriers and then filling the mixture into hardened gelatin capsules, soft capsules, or the like.

Useful carriers for use in suppositories include, for example, polyethylene glycol, cacao butter, higher alcohols, esters of higher alcohols, gelatin, and semisynthetic glyceride.

When the preparation is prepared in the form of an injection, the injection solution, emulsion or suspension is sterilized and preferably isotonic with blood. Useful diluents for preparing the injection include, for example, water, ethyl alcohol, macrogol, propylene glycol, ethoxylated isostearyl alcohol, polyoxylated isostearyl alcohol, and polyoxyethylene sorbitan fatty acid esters. The injection may contain sodium chloride, glucose, or glycerin in an amount sufficient to make an isotonic solution. Also, an ordinary solubilizer, buffer, soothing agent or the like can be added to the injection.

Further, the preparation of the present invention in any of the above forms may contain a pharmaceutically acceptable additive, such as a color, preservative, flavor, odor improver, taste improver, sweetener, or stabilizer. The above carriers and additives may be used either singly or in combination.

The amount of the isotope-labeled pyrimidine compound or pyrimidine metabolic compound (active ingredient) per unit dose of the preparation of the present invention varies depending on the test sample and the kind of active ingredient used, and cannot be generally defined. Thus, the amount can be suitably adjusted and established according to the case. For example, isotope-labeled uracil, such as 2-$^{13}$C-labeled uracil, is used as an isotope-labeled pyrimidine compound (active ingredient), each unit dose of the preparation contains 1 to 1000 mg/body, preferably 10 to 100 mg/body, of the isotope-labeled uracil. When another isotope-labeled pyrimidine compound or pyrimidine metabolic compound is used as an active ingredient, its amount can be adjusted according to the above range. When an isotope-labeled fluorouracil drug, such as isotope-labeled 5-fluorouracil or 5-fluorouracil precursor, is used as the isotope-labeled pyrimidine compound, the drug is preferably administered in an amount such that the pharmacological effect of the drug does not adversely influence the subject. A preferred amount is, for example, 1 to 300 mg/body per unit dose, although it is not limited thereto as long as the above condition is satisfied.

When the preparation of the present invention is administered to a subject with a normal pyrimidine capacity in whom/which the series of pyrimidine metabolizing enzymes (DPD, DPHase and β-UPase) function normally (hereinafter sometimes referred to as "healthy subject"), the pyrimidine compound contained as an active ingredient in the preparation is metabolically degraded as shown in FIG. 1.

For example, uracil, 5-fluorouracil (5-FU), or thymine as the pyrimidine compound is degraded in vivo into dihydrouracil, 5-fluorodihydrouracil (FDHU), or dihydrothymine, respectively, by the action of DPD (the first enzyme in the pyrimidine metabolic pathway), then into β-ureidopropionic acid, fluoro-β-ureidopropionic acid (F-β-UPA), or β-ureidoisobutyric acid, respectively, by the action of DHPase (the second enzyme in the pyrimidine metabolic pathway), and further into β-alanine, fluoro-β-alanine (F-β-alanine), or β-aminoisobutyric acid, respectively, and $CO_2$, by the action of β-UPase (the third enzyme in the pyrimidine metabolic pathway).

When the preparation comprises, as an active ingredient, a pyrimidine metabolic compound that acts as a substrate for DHPase, such as dihydrouracil, FDHU, or dihydrothymine (first metabolic compound), the compound is degraded in a healthy subject into β-ureidopropionic acid, F-β-UPA, or β-ureidoisobutyric acid by the action of DHPase, and further into β-alanine, F-β-alanine, or β-aminoisobutyric acid, and $CO_2$, by the action of β-UPase (third enzyme).

When the preparation comprises, as an active ingredient, a pyrimidine metabolic compound that acts as a substrate for β-UPase, such as β-ureidopropionic acid, F-β-UPA, or β-ureidoisobutyric acid (second metabolic compound), the compound is degraded in a healthy subject into β-alanine, F-β-alanine, or β-aminoisobutyric acid, and $CO_2$, by the action of β-UPase.

The final metabolite $CO_2$ is excreted in the expired air, and β-alanine, F-β-alanine, or β-aminoisobutyric acid is excreted mainly in the urine. When excreted, at least one of the final metabolites ($CO_2$, β-alanine, F-β-alanine, or β-aminoisobutyric acid) is labeled with an isotope, according to the isotope-labeled site of the pyrimidine compound or pyrimidine metabolic compound used as an active ingredient. Therefore, the isotope label is used as an index to measure the excretion behavior (the behavior of excretion amount or excretion rate with the lapse of time) of the final metabolite in a test sample (the expired air when $CO_2$ is labeled, or the urine when β-alanine, F-β-alanine, or β-aminoisobutyric acid is labeled).

Using the preparation of the present invention, the pyrimidine metabolic capacity in an individual subject can be determined and assessed by measuring the excretion behavior (the behavior of excretion amount and excretion rate with the lapse of time) of the above final metabolites.

Specifically, the preparation of the present invention is administered via the oral or parenteral route to a subject and an isotope-labeled metabolite excreted from the body is measured, so that the pyrimidine metabolic capacity (existence, nonexistence, or degree of pyrimidine metabolic disorder (decrease/increase)) in the subject can be determined from the obtained excretion behavior (the behavior of excretion amount and excretion rate with the lapse of time) of the isotope-labeled metabolite.

The metabolite excreted from the body varies depending on the kind of the active ingredient used in the preparation. For example, when the preparation comprises isotope-labeled uracil or isotope-labeled uracil precursor as an active ingredient, the final metabolite is isotope-labeled β-alanine or isotope-labeled $CO_2$. When the preparation comprises isotope-labeled 5-fluorouracil or 5-fluorouracil precursor (prodrug) as an active ingredient, the final metabolite is isotope-labeled fluoro-β-alanine or isotope-labeled $CO_2$. When the preparation comprises isotope-labeled thymine or isotope-labeled thymine precursor as an active ingredient, the final metabolite is isotope-labeled β-aminoisobutyric acid or isotope-labeled $CO_2$.

Preferably, the preparation comprises, as an active ingredient, an isotope-labeled pyrimidine compound or isotope-labeled precursor of a pyrimidine compound that enables the excretion of isotope-labeled $CO_2$ in the expired air as a result of metabolism. Using such a preparation, the pyrimidine metabolic capacity (existence, nonexistence, or degree of pyrimidine metabolic disorder (decrease/increase)) in a subject can be determined from the excretion behavior (the behavior of excretion amount and excretion rate with the lapse of time) of isotope-labeled $CO_2$, which is obtained by administering the preparation to the subject via the oral or parenteral route and measuring isotope-labeled $CO_2$ excreted in the expired air.

When the preparation comprises, as an active ingredient, a pyrimidine compound that produces an isotope-labeled compound other than isotope-labeled $CO_2$, such as β-alanine, fluoro-β-alanine, or β-aminoisobutyric acid, excrement such as the urine or sweat is used in place of the expired air as the test sample.

The pyrimidine metabolic capacity in a subject can be assessed by, for example, comparing the excretion behavior (the behavior of excretion amount or excretion rate with the lapse of time) of an isotope-labeled metabolite obtained by the above measurement, with the excretion behavior of the isotope-labeled metabolite in a healthy subject with a normal pyrimidine metabolic capacity, which is measured in the same manner. Further, in place of or in addition to the excretion behavior of an isotope-labeled metabolite, the area under the curve (AUC), excretion rate (in particular, initial excretion rate), maximum excretion concentration (Cmax), or a similar parameter, preferably pharmacokinetic parameter, obtained from the excretion behavior (transition curve of the excretion amount) in the subject is compared with the corresponding parameter in a healthy subject.

The deficiency or existence of a pyrimidine metabolizing enzyme (at least one of DPD, DHPase, and β-UPase) can be determined by the nonexistence or existence of the excretion of the isotope-labeled metabolite, without comparison with the excretion behavior in a healthy subject. Also, the existence or nonexistence of a decrease or increase in pyrimidine metabolic capacity (pyrimidine metabolic disorder) and the degree of the disorder in a subject can be determined by comparing the excretion behavior in the subject or a parameter obtained therefrom, with the corresponding excretion behavior or parameter in a healthy subject.

When an excretion, such as the urine or sweat, is used as the test sample, the isotope-labeled pyrimidine compound (or an isotope-labeled pyrimidine metabolic compound), isotope-labeled intermediate metabolites, and isotope-labeled final metabolite that are contained in the test sample can be separated simultaneously and analyzed at a time by the combined use of separation techniques, such as liquid chromatography and gas chromatography. Thus, the excretion behavior of the isotope-labeled metabolites can be selectively measured.

The pyrimidine metabolic pathway consists of three steps of enzyme reactions with a series of pyrimidine metabolizing enzymes (DPD, DHPase, and β-UPase), as described above. The pyrimidine metabolic capacity in a subject can be assessed using a preparation comprising the substrate for the first enzyme (DPD) in the pyrimidine metabolic pathway, or its precursor (either of which is labeled with an isotope) as an active ingredient, from the excretion behavior of the final metabolite obtained by administering the preparation. In this case, the deficiency or existence of the first enzyme (DPD), or the degree of decrease or increase (disorder) of its activity in the subject can be assessed by taking the pyrimidine metabolic capacity based on the second enzyme (DHPase) and the third enzyme (β-UPase) into account. The pyrimidine metabolic capacity based on the second enzyme (DHPase) and the third enzyme (β-UPase) can be found by: administering a preparation for measuring pyrimidine metabolic capacity comprising a substrate for the second enzyme (DPHase) (isotope-labeled compound) as an active ingredient to a subject; measuring the final metabolite excreted from the body; and assessing the excretion behavior (the behavior of excretion amount, excretion rate, or the like with the lapse of time) obtained by the measurement.

The pyrimidine metabolic capacity based on the second enzyme (DPD) in a subject can be assessed from the excretion behavior (the behavior of excretion amount, excretion rate, or the like with the lapse of time) of the final metabolite obtained by administering a preparation comprising a substrate for the second enzyme (DHPase) (isotope-labeled compound). In this case, the pyrimidine metabolic capacity based on the third enzyme (β-UPase) in the pyrimidine metabolic pathway in the subject is taken into account. The pyrimidine metabolic capacity based on the third enzyme (β-UPase) can be found by: administering a preparation comprising a substrate for the third enzyme (β-UPase) (isotope-labeled compound) to a subject; measuring the final metabolite excreted from the body; and assessing the obtained excretion behavior (the behavior of excretion amount, excretion rate, or the like with the lapse of time).

The preparation of the present invention can be suitably used for detecting the existence or nonexistence of a pyrimidine metabolic disorder (decrease/increase) in an individual subject, or for measuring and assessing the degree of the disorder. In particular, a preparation comprising, as an active ingredient, a substrate for DPD, such as uracil, thymine, or a derivative thereof (e.g., 5-fluorouracil), which is labeled with an isotope, can be suitably used for measuring and assessing the existence, deficiency, or degree of pyrimidine metabolic disorder (decrease/increase) based on the deficiency of DPD or decrease or increase of its activity in an individual subject. Therefore, the preparation for determining pyrimidine metabolic capacity according to the present invention can also be expressed as a preparation for detecting a pyrimidine metabolic disorder, a preparation for measuring a pyrimidine metabolic disorder, a preparation for diagnosing a pyrimidine metabolic disorder, or the like.

(2) Method for Determining Pyrimidine Metabolic Capacity

The present invention also provides a method for determining the pyrimidine metabolic capacity in a subject. This method can be easily carried out using the preparation for determining pyrimidine metabolic capacity described above.

Specifically, the pyrimidine metabolic capacity in a subject can be determined as follows. The preparation described above is administered to an animal (especially mammal) or human subject whose pyrimidine metabolic capacity is to be determined. Then, the expired air, urine, sweat, or another excretion is collected as a test sample, and the excretion behavior (the behavior of excretion amount or excretion rate with the lapse of time) of an isotope-labeled metabolite is measured from the amount of the isotope-labeled metabolite excreted in the sample.

The isotope-labeled metabolite in the test sample can be measured and analyzed by a conventional analysis technique, such as liquid scintillation counting, mass spectroscopy, infrared spectroscopic analysis, emission spectrochemical analysis, or nuclear magnetic resonance spectral analysis, which is selected depending on whether the isotope used is radioactive or non-radioactive.

Pyrimidine metabolism in vivo is effected by a series of pyrimidine metabolizing enzymes. A pyrimidine compound or pyrimidine metabolic compound taken in the body is metabolized mainly by the pyrimidine metabolizing enzymes into $CO_2$ and other metabolites (β-alanine, fluoro-β-alanine, β-aminoisobutyric acid, and the like.), and excreted from the body. Thus, preferred examples of the isotope-labeled metabolites to be measured include isotope-labeled $CO_2$, isotope-labeled β-alanine, isotope-labeled fluoro-β-alanine, and isotope-labeled β-aminoisobutyric acid.

The sample for use in the measurement method of the present invention can be selected according to the type of isotope-labeled metabolite produced depending on the isotope-labeled site in the administered pyrimidine compound or pyrimidine metabolic compound. Therefore, a suitable sample is the expired air when the isotope-labeled metabolite is $CO_2$, and the urine when the isotope-labeled metabolite is β-alanine, fluoro-β-alanine, or β-aminoisobutyric acid. The expired air is preferred from the viewpoint of ease of sample collection, and the urine is preferred from the viewpoint of feasibility of simultaneously analyzing the final and intermediate metabolites.

The present invention further provides, as a preferred method for determining pyrimidine metabolic capacity, a method comprising administering the preparation for determining pyrimidine metabolic capacity to a subject, and measuring the excretion behavior (the behavior of excretion amount and excretion rate with the lapse of time) of isotope-labeled $CO_2$ excreted in the expired air.

This preferred method uses a preparation comprising as an active ingredient an isotope-labeled pyrimidine compound or pyrimidine metabolic compound designed to produce isotope-labeled $CO_2$ as a final metabolite. Specific examples of such isotope-labeled pyrimidine compounds include compounds having isotope-labeled carbon at the 2-position of the pyrimidine skeleton, preferably 2-$^{13}$C-labeled uracil or 2-$^{13}$C-labeled 5-fluorouracil, more preferably 2-$^{13}$C-labeled uracil.

When $^{13}$C is used as an isotope, the amount of $^{13}CO_2$ excreted in the expired air can be measured by conventional $^{13}$C-Breath Tests (Bunseki Kagaku (Analytical Chemistry), Vol. 31, pp. 450-453 (1982); HELICOBACTER, vol. 3, No. 1, pp. 49-53 (1998), etc.).

The pyrimidine metabolic capacity in each subject can be assessed based on the excretion behavior (the behavior of excretion amount or excretion rate with the lapse of time) of an isotope-labeled metabolite measured by the above method. Specifically, the pyrimidine metabolic capacity in each subject can be assessed by: administering the preparation of the present invention to the subject; measuring the excretion behavior (the behavior of excretion amount or excretion rate with the lapse of time) of an isotope-labeled metabolite in the urine, expired air or another excretion; and comparing the excretion behavior thus obtained with the corresponding excretion behavior in a healthy subject.

Preferably, a preparation comprising 2-$^{13}$C-labeled uracil or 2-$^{13}$C labeled 5-fluorouracil as an active ingredient is administered to a subject, the excretion behavior of isotope-labeled $CO_2$ excreted in the expired air of the subject is measured, and the obtained excretion behavior is compared with the corresponding excretion behavior of isotope-labeled $CO_2$ in a healthy subject. Specifically, the excretion behavior (the behavior of excretion amount or excretion rate with the lapse of time) of isotope-labeled $CO_2$ (e.g., $^{13}CO_2$) in the expired air can be visually shown in the following manner: after administering the preparation of the present invention to a subject, the ratio of $^{13}CO_2$ to $^{12}CO_2$ (the $^{13}CO_2/^{12}CO_2$ concentration ratio: $\delta^{13}C$ value) in the expired air is measured over the lapse of time, and the carbon dioxide $\Delta(‰)$ value is calculated from the difference between the measured $\delta^{13}C$ value and the $\delta^{13}C$ value in the subject before administration of the preparation, and then the $\Delta(‰)$ value is plotted against the expired air collection time (the time elapsed after administration of the preparation) to make a graph. For comparison of the excretion behavior of isotope-labeled $CO_2$ in the subject with that of a healthy subject, for example, the above-obtained graph is compared with a graph showing the excretion behavior in a healthy subject, obtained in the same manner as above.

Further, the method of the present invention can be carried out by comparing, in place of or in addition to the excretion behavior of an isotope-labeled metabolite, the area under the curve (AUC), excretion rate (especially the initial excretion rate), the maximum excretion concentration (Cmax), or a similar parameter, preferably a pharmacokinetic parameter, obtained from the excretion behavior (transition curve of the excretion amount: excretion curve) in a subject, with the corresponding parameter in a healthy subject. In this manner, it is possible to assess the existence or nonexistence of a decrease or increase of the pyrimidine metabolic capacity (pyrimidine metabolic disorder) in the subject, or the degree of the disorder.

The deficiency or existence of DPD, the first enzyme of the pyrimidine metabolic pathway, can be determined by the nonexistence or existence of the excretion of an isotope-labeled metabolite, without comparison with the excretion behavior in a healthy subject.

When the urine, sweat or another excretion is used as the test sample, the isotope-labeled pyrimidine compound (or isotope-labeled pyrimidine metabolic compound), isotope-labeled intermediate metabolites, and isotope-labeled final metabolite that are contained in the test sample can be separated simultaneously and analyzed at a time by the combined use of separation techniques, such as liquid chromatography and gas chromatography. Thus, the excretion behavior of the isotope-labeled metabolites can be selectively measured.

As described above, the present invention makes it possible to detect the existence or nonexistence of an disorder (decrease or increase) of the pyrimidine metabolic capacity in an individual subject or measure the degree of the disorder. Therefore, the method of measuring or assessing pyrimidine metabolic capacity according to the present invention can also be defined as a method for detecting the existence or nonexistence of an disorder (decrease/increase) of the pyrimidine metabolic capacity in an individual subject, a method for measuring the degree of an disorder (decrease/increase) of the pyrimidine metabolic capacity in a subject, or a method for assessing the existence, nonexistence, or degree of an disorder (decrease or increase) of the pyrimidine metabolic capacity in a subject.

(3) Method for Screening a Subject for Suitability for Fluorouracil Drug Administration From the pyrimidine metabolic capacity in a subject assessed by the method of the present invention, the suitability of the subject for the administration of various fluorouracil drugs can be predicted. Thus, the present invention provides a method for screening a subject for suitability for fluorouracil drug administration. The subject suitable for fluorouracil drug administration according to the present invention is preferably a subject (an animal (mammal) including a human, preferably a human) in whom/which the administration of a fluorouracil drug, such as 5-FU or its prodrug, achieves the therapeutic effects usually expected based on the common knowledge in this field, without severe side effects. In a broad sense, the subject suitable for fluorouracil drug administration includes a subject (an animal (mammal) including a human) in whom/which fluorouracil drug administration causes no severe side effects, or in whom/which the therapeutic effects of a fluorouracil drug is expected.

The screening method of the present invention can be carried out by performing the method for measuring and assessing pyrimidine metabolic capacity according to the present invention, on a subject to be given a pyrimidine drug (a subject to be treated with a pyrimidine drug), such as a cancer patient. Specifically, the preparation of the present invention is administered to the subject; an excretion, such as the expired air or urine, is collected as a test sample; the excretion behavior (the behavior of excretion amount or excretion rate with the lapse of time) of an isotope-labeled metabolite excreted in the test sample is measured; and the suitability of the subject for fluorouracil drug administration is determined based on the obtained excretion behavior.

For example, when the excretion of the isotope-labeled metabolite is not observed in a subject, it can be determined that the subject lacks pyrimidine metabolic capacity because of the deficiency in a pyrimidine metabolizing enzyme (at least one of DPD, DHPase, and β-UPase) in the pyrimidine metabolic pathway, and therefore is unsuitable for fluorouracil drug administration. When the excretion of the isotope-labeled metabolite is observed in a subject, the suitability of the subject for fluorouracil drug administration can be determined by comparing the excretion behavior of the isotope-labeled metabolite in the subject or a pharmacokinetic parameter obtained therefrom with the corresponding excretion behavior or parameter in a healthy subject. When the pyrimidine metabolic capacity in the subject assessed from the excretion behavior or its parameter is extremely lower than the pyrimidine metabolic capacity in a healthy subject, side effects are expected. On the other hand, when the pyrimidine metabolic capacity in the subject is notably higher than that in a healthy subject, the desired therapeutic effect cannot be achieved. In both cases, it is determined that the subject is not suitable for fluorouracil drug administration.

Further, when the correlation (correlation diagram) between a pharmacokinetic parameter based on the excretion behavior of an isotope-labeled metabolite and the pyrimidine metabolic capacity (preferably, the pyrimidine metabolic capacity determined by a method other than the method of the present invention), more preferably the correlation (correlation diagram) between a pharmacokinetic parameter and the suitability for fluorouracil drug administration, in a large number of randomly selected subjects is found in advance, the suitability of a subject for fluorouracil drug administration can be determined by applying the parameter based on the excretion behavior measured by the method of the present invention to the correlation diagram.

It also becomes possible to determine the clearance of a fluorouracil drug in a subject from the pyrimidine metabolic capacity in the subject assessed by the method of the present invention, or to establish a dosage regimen (formula (type, composition, etc.), dose, number of doses, and the like) of a fluorouracil drug.

Specifically, the pyrimidine metabolic capacity in a subject (a patient to be given a fluorouracil drug) is assessed by the above assessment method before administration of the fluorouracil drug, so that the clearance of the fluorouracil drug can be determined from the pyrimidine metabolic capacity, and the dosage regimen (formula (type, composition, etc.), dose, number of doses, and the like) of the fluorouracil drug can be established based on the clearance. Examples of fluorouracil drugs include 5-fluorouracil, tegafur, carmofur, doxifluridine, and the like, which have been used as anticancer drugs.

In this manner, the capacity of degrading a fluorouracil drug in a subject can be assessed in advance, making it possible to predict the risk of the side effects of the fluorouracil drug in a patient with a pyrimidine metabolic disorder, such as DPD deficiency or DPD activity reduction, to prevent the side effects. Thus, the method of the present invention is useful as a method for preventing the side effects that may be caused by administration of a fluorouracil drug.

EXAMPLES

The following examples are provided to illustrate the present invention in further detail, and are not intended to limit the scope of the claims herein.

Example 1

Uracil having $^{13}$C-labeled carbon at the 2-position (2-$^{13}$C-labeled uracil) was used as an isotope-labeled pyrimidine compound. A preparation for determining the pyrimidine metabolic capacity in the form of an intravenous injection comprising the 2-$^{13}$C-labeled uracil as an active ingredient was prepared and tested for usefulness for determining pyrimidine metabolic capacity.

(1) Production of a Preparation for Determining Pyrimidine Metabolic Capacity

Uracil-2-$^{13}$C (Cambridge Isotope Laboratory) (300 mg) was dissolved in 24 ml of 0.1N NaOH/saline solution (measured out from 200 ml of 0.1N NaOH/saline solution prepared by diluting 2 ml of 10N sodium hydroxide solution with physiological saline), to give a preparation for determining the pyrimidine metabolic capacity in the form of an intravenous injection (containing 50 mg of uracil-2-$^{13}$C per 4 ml of the injection).

(2) Preparation of (E)-5-(2-bromovinyl)-uracil Preparation (E)-5-(2-bromovinyl)-uracil is known as a dihydropyrimidine dehydrogenase (DPD) inhibitor (Cancer Research 46, 1094-1101, Mar. 1986, pp.1094-1101). (E)-5-(2-bromovinyl)-uracil (250 mg) and gum arabic (2.25 g) were mixed together, and the mixture was kneaded while adding a slight amount of water, to prepare 45 ml of a suspension (containing 83.3 mg of (E)-5-(2-bromovinyl)-uracil per 15 ml of the suspension).

(3) Experiment

Fasted beagle dogs were used as experimental animals. In Group 1 (n=3), the preparation for determining pyrimidine metabolic capacity prepared above was intravenously injected (50 mg/body) (test group). In Group 2 (n=3), the (E)-5-(2-bromovinyl)-uracil preparation (DPD inhibitor) was first administered orally (83.3 mg/body), and after 1 hour, the preparation for determining pyrimidine metabolic capacity was intravenously injected (50 mg/body) in the same manner as in Group 1 (comparative group: uracil metabolic disorder animal models). In both groups, the expired air was collected before administration of the preparation for determining pyrimidine metabolic capacity and 15, 30, 45, 60, 75, 90, 105, 120, 135, 150, 180, 210, and 240 minutes after administration of the preparation. The concentration of $^{13}$C-labeled carbon dioxide excreted in the collected expired air was measured using a GC-MS analyzer (ABCA-G, Europa Scientific).

Figure 2:
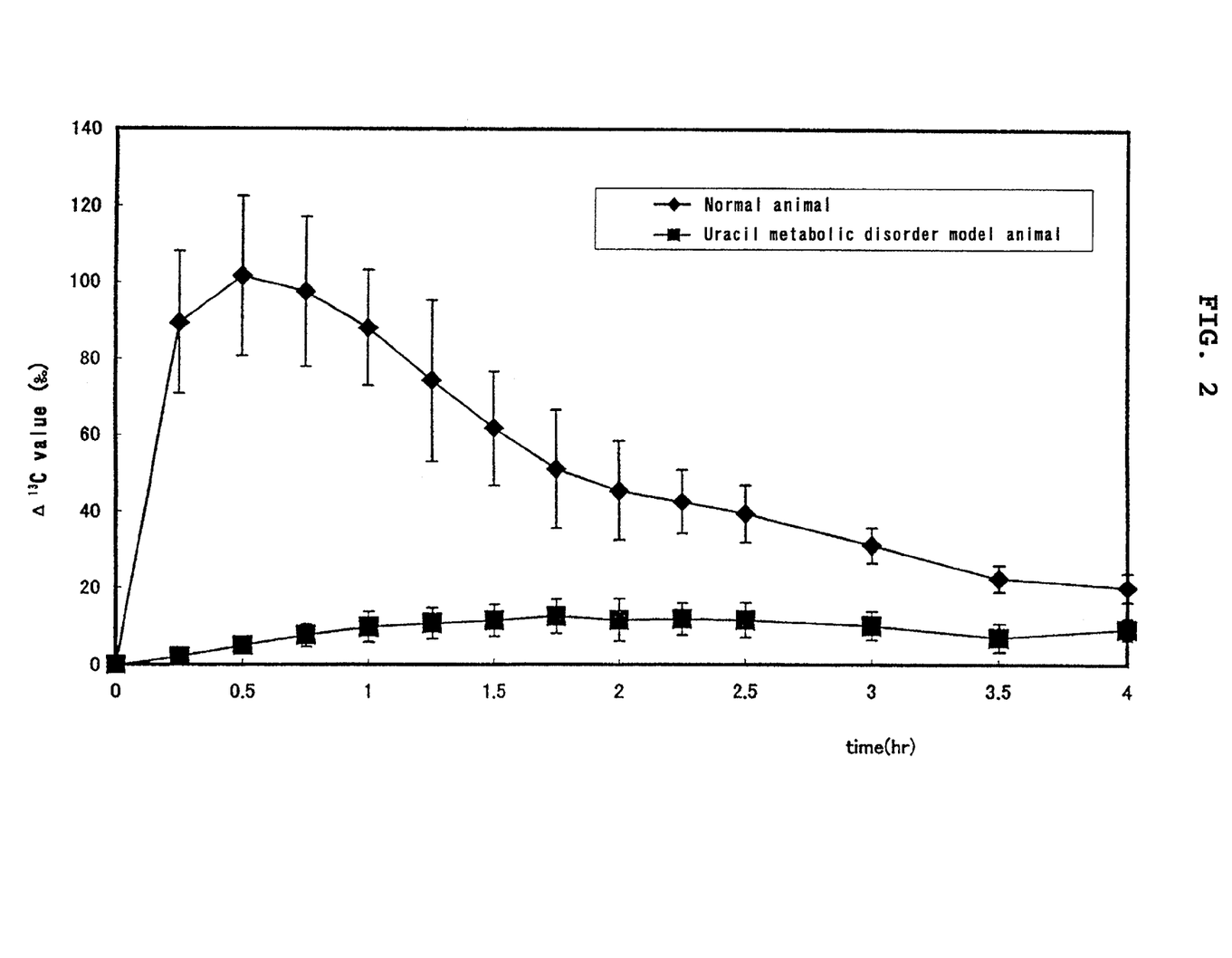
FIG. 2 shows the experiment results obtained in Example 1, in which a preparation for determining pyrimidine metabolic capacity according to the present invention was intravenously administered to experimental animals. In Example 1, after intravenous injection of 2-$^{13}$C-labeled uracil, the behavior of $^{13}CO_2$ excreted in the expired air was observed over the lapse of time in healthy animals (-♦-) and in model animals with uracil metabolic disorder (-■-). The time (hr) at which the expired air was collected after administration of the preparation is plotted in abscissa, and the amount of $^{13}CO_2$ excreted in the expired air is plotted in ordinate as a $\Delta^{13}C$ value (‰), i.e., the difference between the $\delta^{13}C$ value (‰) (the $^{13}CO_2/^{12}CO_2$ concentration ratio) in the expired air before administration of the preparation and the $\delta^{13}C$ value (‰) in the expired air at each collection time after administration of the preparation (the same applies to FIGS. 3 and 4).

FIG. 2 shows the results in the test group (-♦-) and those in the comparative group (-■-). In the figure, in ordinate is plotted the $\Delta^{13}$C value (‰), which is the difference in the $\delta^{13}$C value (‰) (the $^{13}CO_2/^{12}CO_2$ concentration ratio in the expired air) between the expired air sample collected before administration of the preparation for determining pyrimidine metabolic capacity and each of the expired air samples collected after administration of the preparation, and in abscissa is plotted the time of collecting the expired air after administration of the preparation.

As is apparent from FIG. 2, in the test group, it was observed that 2-$^{13}$C-labeled uracil was metabolized and excreted in the expired air as $^{13}CO_2$. On the other hand, in the uracil metabolic disorder animal models (comparative group) artificially created by administering a DPD inhibitor beforehand, markedly lower excretion of $^{13}CO_2$ in the expired air was observed. Thus, it was demonstrated that the use of the preparation of the present invention (in an intravenous injection form), which comprises 2-$^{13}$C-labeled uracil as an active ingredient, makes it possible to measure and assess the existence or nonexistence of a uracil metabolic disorder (decrease of uracil metabolic capacity) caused by the inhibition or reduction of DPD activity by inspecting the excretion behavior of $^{13}CO_2$ in the expired air.

Example 2

A preparation for determining the pyrimidine metabolic capacity in an oral form was prepared using the same 2-$^{13}$C-labeled uracil as used in Example 1 as an active ingredient, and tested for usefulness for measuring pyrimidine metabolic capacity.

(1) Production of a Preparation for Determining Pyrimidine Metabolic Capacity

2-$^{13}$C-labeled uracil (Cambridge Isotope Laboratory) (300 mg) was dissolved in 24 ml of 0.1N NaOH/saline solution (measured out from 200 ml of 0.1N NaOH/saline solution prepared by diluting 2 ml of 10N sodium hydroxide solution with physiological saline). Then, water was added to give 60 ml of a preparation for determining pyrimidine metabolic capacity in the form of an oral solution (containing 50 mg of 2-$^{13}$C-labeled uracil per 10 ml of the oral solution).

(2) Experiment

Figure 3:
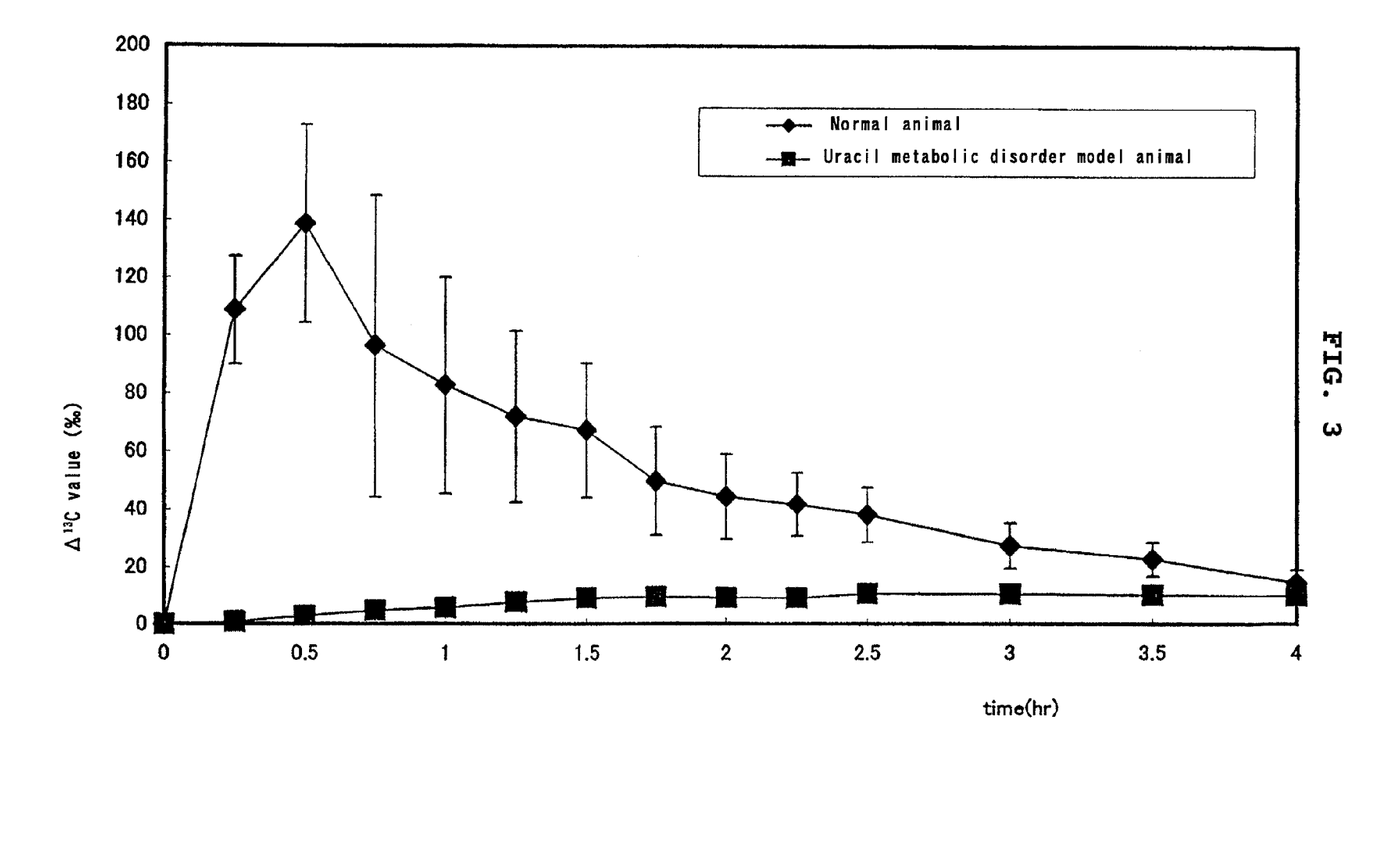
FIG. 3 shows the experiment results obtained in Example 2, in which a preparation for determining pyrimidine metabolic capacity according to the present invention is orally administered to experimental animals. In Example 2, after oral administration of 2-$^{13}$C-labeled uracil, the behavior of $^{13}CO_2$ excreted in the expired air was observed over the lapse of time in healthy animals (-♦-) and in model animals with uracil metabolic disorder (-■-).

Fasted beagle dogs were used as experimental animals. In Group 1 (n=3), the preparation prepared above in (1) was orally administered (50 mg/10 ml/body) (test group). In Group 2 (n=3), the (E)-5-(2-bromovinyl)-uracil preparation (DPD inhibitor) prepared in the same manner as in Example 1 (2) was orally administered (83.3 mg/15 ml/body), and after 1 hours, the preparation for determining pyrimidine metabolic capacity was orally administered (50 mg/10 ml/body) in the same manner as in Group 1 (comparative group: uracil metabolic disorder animal models). In both groups, after oral administration of the preparation for determining pyrimidine metabolic capacity, 10 ml of water was forcibly administered orally using the tube used for administration of the preparation, to wash out the preparation remaining in the tube. In both groups, the expired air was collected before administration of the preparation for determining pyrimidine metabolic capacity and 15, 30, 45, 60, 75, 90, 105, 120, 135, 150, 180, 210, and 240 minutes after administration of the preparation. The concentration of $^{13}$C-labeled carbon dioxide excreted in the expired air was measured in the same manner as in Example 1, using a GC-MS analyzer (ABCA-G, Europa Scientific). FIG. 3 shows the results in the test group (-♦-) and those in the comparative group (-■-). In FIG. 3, the definitions of abscissa and ordinate are the same as those in Example 1.

As is apparent from FIG. 3, in the test group, when the preparation of the present invention was administered orally, it was observed that 2-$^{13}$C-labeled uracil was metabolized and excreted in the expired air as $^{13}CO_2$, like in the case of intravenous administration (Example 1). On the other hand, in the uracil metabolic disorder animal models artificially created by administering a DPD inhibitor beforehand (comparative group), the excretion of $^{13}CO_2$ in the expired air was markedly reduced. Thus, it was demonstrated that the use of the preparation of the present invention (in an oral form), which comprises 2-$^1$C-labeled uracil as an active ingredient, makes it possible to measure and assess the existence or nonexistence of a uracil metabolic disorder (decrease of uracil metabolic capacity) caused by the inhibition or reduction of DPD activity by inspecting the excretion behavior of $^{13}CO_2$ in the expired air.

The results obtained in Examples 1 and 2 prove that the preparation of the present invention is useful for easily and precisely determining the existence or nonexistence of a pyrimidine metabolic disorder (decrease or increase of pyrimidine metabolic ability) in vivo using the expired air, regardless of its dosage form.

Example 3

In 50 ml portions of 0.05N sodium hydroxide, 56.5 mg, 113.1 mg, 226.2 mg, and 452.3 mg of 2-$^{13}$C-labeled uracil (Cambridge Isotope Laboratory) were dissolved separately, to prepare solutions with concentrations of 10 μmol/ml, 20 μmol/ml, 40 μmol/ml, and 80 μmol/ml, respectively. The solutions were forcibly administered orally to fasted male beagle dogs (n=3) using oral tubes for dogs, in an amount of 1 ml/kg body weight (dose: 10, 20, 40, and 80 μml/kg), and thereafter water was forcibly administered orally in an amount of 2 ml/kg body weight. The expired air was collected before administration, and after 15, 30, 45, 60, 75, 90, 105, 120, 135, 150, 180, 210, and 240 minutes after administration. Then, the $^{13}$C-labeled carbon dioxide concentration in the expired air was measured, and pharmacokinetic parameters (the area under the curve (AUC) and maximum $^{13}$C-labled carbon dioxide concentration (Cmax)) were calculated from the obtained transition curve of the $^{13}$C-labeled carbon dioxide concentration in the expired air.

Figure 4:
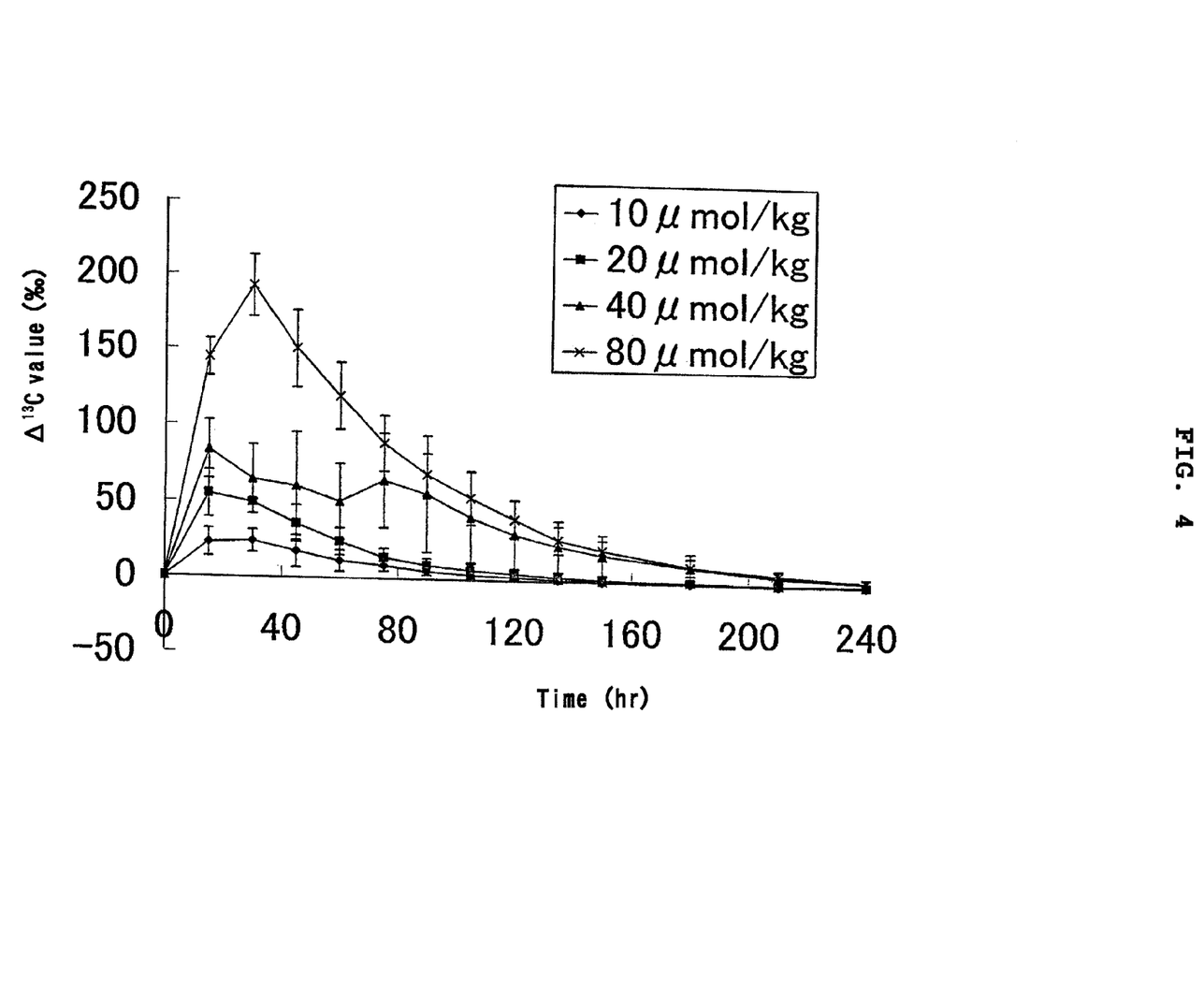
FIG. 4 shows the experiment results obtained in Example 3, in which preparations for determining pyrimidine metabolic capacity that contain 2-$^{13}$C-labeled uracil at various concentrations are orally administered to experimental animals, and the behavior of $^{13}CO_2$ excreted in the expired air ($\Delta^{13}C$ value (‰)) was observed over the lapse of time. The doses of 2-$^{13}$C-labeled uracil were as follows: 10 μmol/kg body weight (-●-), 20 μmol/kg body weight (-■-), 40 μmol/kg body weight(-▲-), and 80 μmol/kg body weight (-X-).
Figure 5:
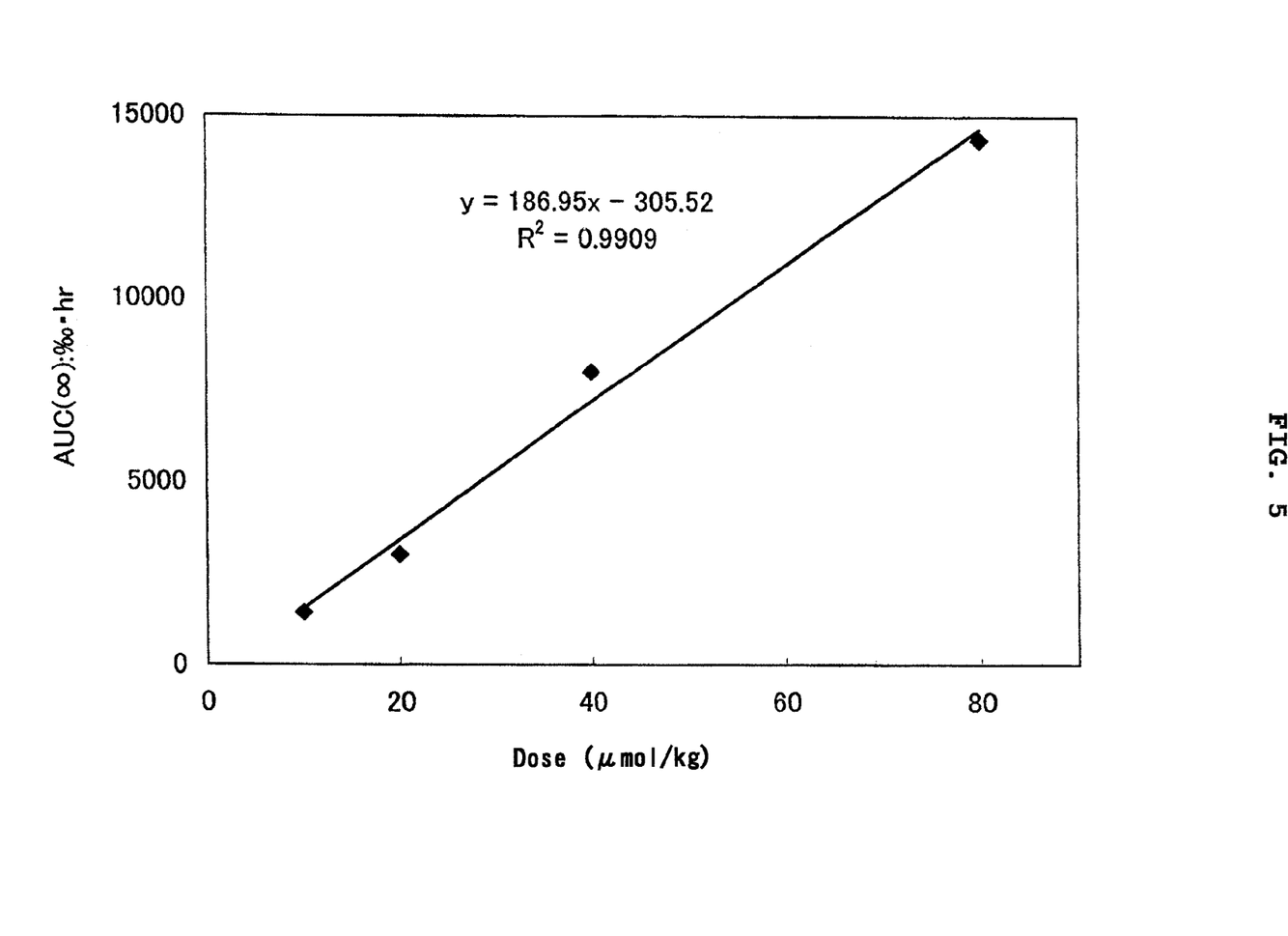
FIG. 5 is a graph in which the dose (μmol/kg body weight) of 2-$^{13}$C-labeled uracil is plotted in abscissa, and the area under the curve (AUC: ‰·hr) at each dose of 2-$^{13}$C-labeled uracil determined from the results obtained in Example 3 (FIG. 4) is plotted in ordinate.
Figure 6:
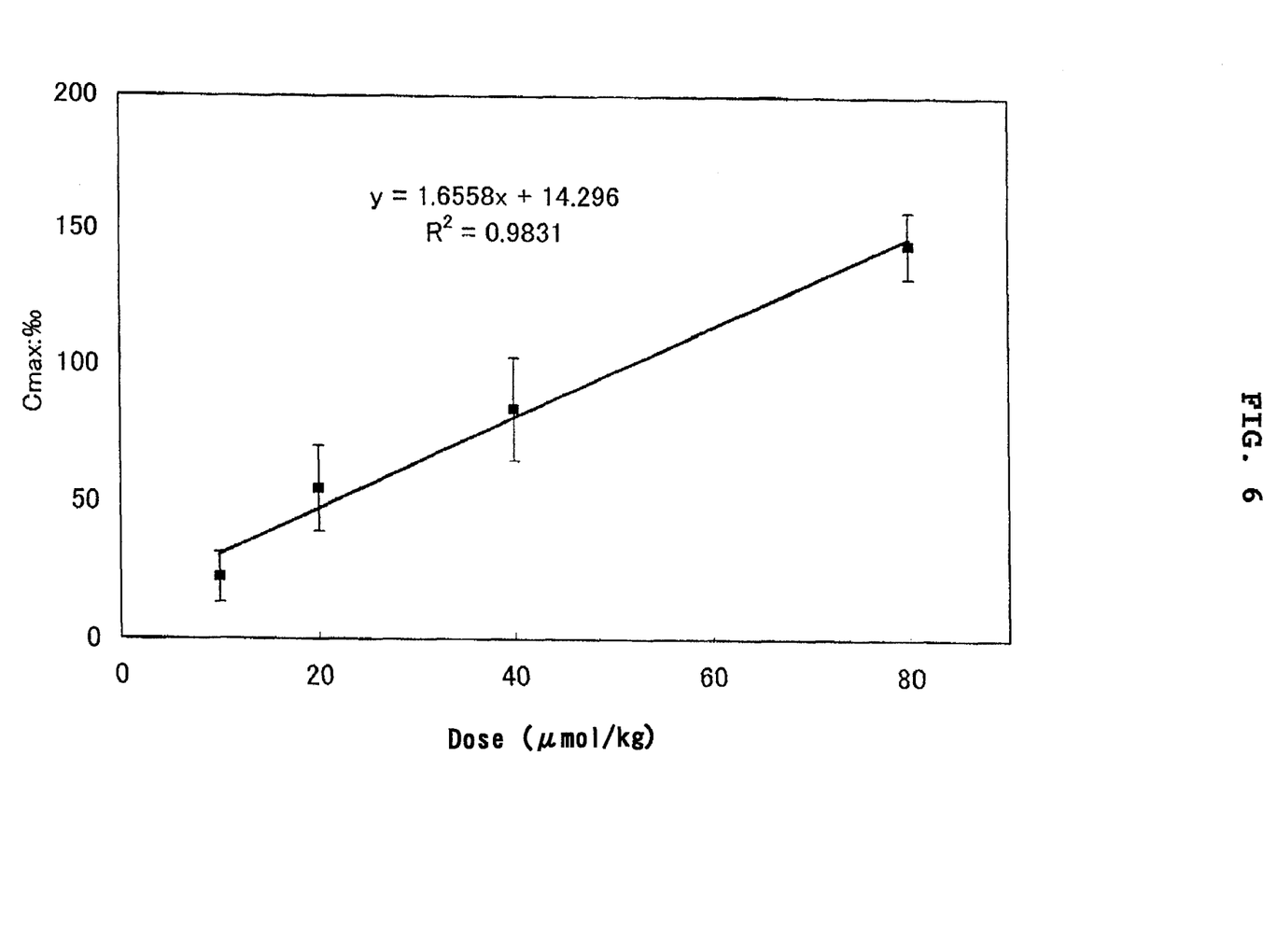
FIG. 6 is a graph in which the dose (μmol/kg body weight) of 2-$^{13}$C-labeled uracil is plotted in abscissa, and the maximum $^{13}CO_2$ concentration (Cmax) in the expired air at each dose of 2-$^{13}$C-labeled uracil determined from the results obtained in Experiment 3 (FIG. 4) is plotted in ordinate.

FIG. 4 shows the transition curve of the $^{13}$C-labeled carbon dioxide concentration in the expired air. FIGS. 5 and 6 shows the relation between the dose (μmol/kg body weight) and the area under the curve (AUC), and the relation between the dose and the maximum $^{13}$C-labeled carbon dioxide concentration (Cmax) in the expired air, respectively.

FIG. 4 reveals that the $^{13}$C-labeled carbon dioxide in the expired air reached the maximum concentration 15 to 30 minutes after administration, and then rapidly decreased. As shown in FIGS. 5 and 6, the plots of AUC and Cmax versus dose are straight lines nearly passing through the origin, indicating the linear correlation between the dose and AUC, and between the dose and Cmax. This means that the excretion kinetics of 2-$^{13}$C-labeled uracil in the expired air has linearity at a dose of 10 to 80 μmol/kg body weight.

When a preparation of the present invention comprising 2-$^{13}$C-labeled uracil in an amount of 40 μmol/kg body is orally administered to a subject with an unknown pyrimidine metabolic capacity, and the maximum $^{13}$C-labeled carbon dioxide concentration (Cmax) is measured from the $^{13}$C-labeled carbon dioxide concentration in the expired air and found to be 50‰, it can be determined from FIG. 6 that the pyrimidine metabolic capacity in the subject is reduced to about ½ of the normal pyrimidine metabolic capacity. (In FIG. 6, Cmax=50‰ corresponds to the case where 2-$^{13}$C-labeled uracil is administered in an amount of 20 μmol/kg body weight.)

Formulation Example 1

Mannitol (1400 mg) and 2-$^{13}$C-labeled uracil (Cambridge Isotope Laboratory) (100 mg) were mixed together and formulated into granules in a routine manner.

Formulation Example 2

Mannitol (900 mg) and 2-$^{13}$C-labeled uracil (Cambridge Isotope Laboratory) (100 mg) were mixed together and formulated into subtle granules.

INDUSTRIAL APPLICABILITY

The preparation or method for determining pyrimidine metabolic capacity according to the present invention makes it possible to non-invasively assess the pyrimidine metabolic capacity in an individual subject, using the expired air. Specifically, the preparation and method of the present invention can be suitably used for detecting the existence or nonexistence of a pyrimidine metabolic disorder (decrease/increase) caused by the deficiency of a pyrimidine metabolizing enzyme or an decrease or increase of its activity, or for measuring and assessing the degree of the disorder. Thus, the therapeutic effect or side effects of a fluorouracil drug, such as 5-fluorouracil, can be predicted by assessing the pyrimidine metabolic capacity in a subject using the preparation or method of the present invention. In other words, the preparation and method of the present invention are useful for screening a subject for suitability for fluorouracil drug administration. This screening prevents severe side effects that may be caused by the drug. Further, a fluorouracil drug dosage regimen suitable for an individual subject can be established based on the pyrimidine metabolic capacity determined using the preparation or method of the present invention. Therefore, the preparation and method of the present invention can contribute to a safe, effective therapy (cancer therapy) with a fluorouracil drug.

The invention claimed is:

1. A method for quantitatively determining DPD (dihydropyrimidine dehydrogenase) activity, comprising:
   administering to a subject a preparation comprising an amount of 2-$^{13}$C-labeled uracil as an active ingredient,
   measuring the excretion behavior of an isotope-labeled metabolite of 2-$^{13}$C-labeled uracil excreted from the body,
   determining a pharmacokinetic parameter from the measured excretion behavior, wherein the pharmacokinetic parameter is selected from area under the curve (AUC), initial excretion rate, and maximum excretion concentration ($C_{max}$),
   comparing the pharmacokinetic parameter with the corresponding parameter of a subject having a normal DPD activity characterized by a linear relationship between the pharmacokinetic parameter and the amount of the preparation administered, and
   quantitatively determining DPD activity from the compared pharmacokinetic parameter.

2. A method for quantitatively determining DPD (dihydropyrimidine dehydrogenase) activity, comprising:
   administering to a subject a preparation comprising an amount of 2-$^{13}$C-labeled uracil as an active ingredient,
   measuring the excretion behavior of isotope-labeled $CO_2$ in expired air,
   determining a pharmacokinetic parameter from the measured excretion behavior, wherein the pharmacokinetic parameter is selected from area under the curve (AUC), initial excretion rate, and maximum excretion concentration ($C_{max}$),
   comparing the pharmacokinetic parameter with the corresponding parameter of a subject having a normal DPD activity, characterized by a linear relationship between the pharmacokinetic parameter and the amount of the preparation administered, and quantitatively determining DPD activity from the compared pharmacokinetic parameter.

3. A method for determining the degree of reduction of DPD (dihydropyrimidine dehydrogenase) activity in a subject, comprising:

administering to a subject a preparation comprising an amount of 2-$^{13}$C-labeled uracil as an active ingredient, measuring the excretion behavior of an isotope-labeled metabolite of 2-$^{13}$C-labeled uracil excreted from the body, determining a pharmacokinetic parameter from the measured excretion behavior, wherein the pharmacokinetic parameter is selected from area under the curve (AUC), initial excretion rate, and maximum excretion concentration ($C_{max}$), comparing the pharmacokinetic parameter with the corresponding parameter of a subject having a normal DPD activity characterized by a linear relationship between the pharmacokinetic parameter and the amount of the preparation administered, and assessing the degree of reduction of DPD activity from the assessed compared pharmacokinetic parameter.

4. The method according to claim 3, wherein the isotope-labeled metabolite excreted from the body is isotope-labeled $CO_2$.

5. A method for screening a subject for suitability for fluorouracil drug administration, comprising:

administering to a subject a preparation comprising 2-$^{13}$C-labeled uracil as an active ingredient, measuring the excretion behavior of an isotope-labeled metabolite of 2-$^{13}$C-labeled uracil for at least two time points after the administration, determining a pharmacokinetic parameter from the measured excretion behavior for each time point, wherein the pharmacokinetic parameter is selected from area under the curve (AUC), initial excretion rate, and maximum excretion concentration ($C_{max}$), comparing the pharmacokinetic parameter with the corresponding parameter of a subject with a normal DPD (dihydropyrimidine dehydrogenase) activity characterized by a linear relationship between the pharmacokinetic parameter and the amount of the preparation administered, assessing a degree of reduction of DPD activity in the subject, from the compared pharmacokinetic parameter, and determining the subject's suitability for fluorouracil drug administration based on the assessed degree of reduction of DPD activity.

6. The method according to claim 5, wherein the isotope-labeled metabolite is isotope-labeled $CO_2$.

7. The method according to claim 5, wherein the fluorouracil drug is at least one anticancer drug selected from the group consisting of 5-fluorouracil, tegafur, carmofur, and doxifluridine.

8. The method according to claim 5, wherein in the determination of suitability, the subject is determined as unsuitable when the DPD activity in the subject assessed based on the pharmacokinetic parameter is lower than the corresponding DPD activity in a healthy subject.

9. The method according to claim 6, wherein in the determination of suitability, the subject is determined as unsuitable when the DPD activity in the subject assessed based on the pharmacokinetic parameter is lower than the corresponding DPD activity in a healthy subject.

10. The method according to claim 9, wherein the pharmacokinetic parameter is the area under the curve (AUC) of the isotope-labeled carbon dioxide concentration in expired air.

11. The method according to claim 9, wherein the pharmacokinetic parameter is the maximum isotope-labeled $CO_2$ concentration in expired air.

* * * * *